United States Patent
Acheson et al.

(10) Patent No.: US 9,310,329 B2
(45) Date of Patent: Apr. 12, 2016

(54) REMOTE MOISTURE SENSOR AND METHODS FOR THE SAME

(71) Applicant: Raven Industries, Inc., Sioux Falls, SD (US)

(72) Inventors: John Earl Acheson, Sioux Falls, SD (US); Stephen Filip Fjelstad, Worthing, SD (US); Douglas Samuel Prairie, Sioux Falls, SD (US)

(73) Assignee: Raven Industries, Inc., Sioux Falls, SD (US)

( * ) Notice: Subject to any disclaimer, the term of this patent is extended or adjusted under 35 U.S.C. 154(b) by 37 days.

(21) Appl. No.: 13/835,478

(22) Filed: Mar. 15, 2013

(65) Prior Publication Data

US 2014/0266253 A1 Sep. 18, 2014

(51) Int. Cl.
*G01R 27/26* (2006.01)
*G01N 27/22* (2006.01)
*G01N 33/02* (2006.01)
*A01D 41/127* (2006.01)

(52) U.S. Cl.
CPC .......... *G01N 27/223* (2013.01); *A01D 41/1277* (2013.01); *G01N 33/02* (2013.01)

(58) Field of Classification Search
CPC ...................................... G01N 27/223–27/225
USPC ................................................. 324/664, 694
See application file for complete search history.

(56) References Cited

U.S. PATENT DOCUMENTS

| | | | |
|---|---|---|---|
| 4,376,298 A | 3/1983 | Sokol et al. | |
| 5,092,819 A | 3/1992 | Schroeder et al. | |
| 5,106,339 A * | 4/1992 | Braun et al. | 460/7 |
| 5,343,761 A | 9/1994 | Myers | |
| 5,351,558 A | 10/1994 | Horn et al. | |
| 5,561,250 A * | 10/1996 | Myers | 73/861.73 |
| 5,611,420 A | 3/1997 | Heim et al. | |
| 5,685,772 A | 11/1997 | Andersen et al. | |
| 5,686,671 A | 11/1997 | Nelson et al. | |
| 5,700,961 A * | 12/1997 | Anthony et al. | 73/866 |

(Continued)

FOREIGN PATENT DOCUMENTS

| | | |
|---|---|---|
| DE | 112014001474 T5 | 11/2015 |
| DE | 112014001439 T5 | 1/2016 |

(Continued)

OTHER PUBLICATIONS

"Ag Leader Yield Monitoring", [online]. Retrieved from the Internet: <URL: http://www.agleader.com/products/yield-monitoring/>, (Published Prior to Mar. 15, 2013), 13 pgs.

(Continued)

*Primary Examiner* — Patrick Assouad
*Assistant Examiner* — Demetrius Pretlow
(74) *Attorney, Agent, or Firm* — Schwegman Lundberg & Woessner, P.A.

(57) ABSTRACT

A system for measuring crop moisture content in a harvester elevator includes a receiver and processing node and one or more moisture sensing instruments coupled to one or more paddles of the harvested elevator, respectively. The moisture sensing instruments each include a moisture sensor and a transmitter in communication with a receiver and processing node. The moisture sensor is configured to dynamically measure the moisture content of a static harvested crop, relative to the sensor and corresponding paddle, at ascends in the harvester elevator.

17 Claims, 4 Drawing Sheets

(56) References Cited

U.S. PATENT DOCUMENTS

| | | | |
|---|---|---|---|
| 5,750,877 | A | 5/1998 | Behnke et al. |
| 5,863,247 | A | 1/1999 | Behnke et al. |
| 5,957,773 | A | 9/1999 | Olmsted et al. |
| 5,959,257 | A | 9/1999 | Campbell et al. |
| 6,073,427 | A * | 6/2000 | Nichols ............... 56/10.2 B |
| 6,121,782 | A | 9/2000 | Adams et al. |
| 6,138,518 | A | 10/2000 | Strubbe |
| 6,192,664 | B1 | 2/2001 | Missotten et al. |
| 6,244,782 | B1 | 6/2001 | Bitelli |
| 6,272,935 | B1 | 8/2001 | Strubbe |
| 6,282,967 | B1 | 9/2001 | Homburg et al. |
| 6,283,853 | B1 | 9/2001 | Pellenc et al. |
| 6,285,198 | B1 | 9/2001 | Nelson et al. |
| 6,313,414 | B1 | 11/2001 | Campbell |
| 6,327,899 | B1 * | 12/2001 | Diekhans et al. ............. 73/73 |
| 6,460,008 | B1 | 10/2002 | Hardt |
| 6,508,049 | B1 | 1/2003 | Cox et al. |
| 6,525,276 | B1 | 2/2003 | Vellidus et al. |
| 6,584,424 | B2 * | 6/2003 | Hardt ..................... 702/129 |
| 6,616,527 | B2 * | 9/2003 | Shinners et al. ............. 460/6 |
| 6,669,557 | B2 * | 12/2003 | Adams et al. .............. 460/7 |
| 6,899,616 | B1 | 5/2005 | Murray et al. |
| 6,951,514 | B1 | 10/2005 | Coers et al. |
| 7,340,996 | B1 * | 3/2008 | Viaud ..................... 100/88 |
| 7,412,905 | B1 | 8/2008 | Bishel |
| 7,500,280 | B2 | 3/2009 | Dixon et al. |
| 2002/0133309 | A1 | 9/2002 | Hardt |
| 2003/0033862 | A1 | 2/2003 | Mcelhaney et al. |
| 2005/0225334 | A1 | 10/2005 | Rains et al. |
| 2007/0050116 | A1 | 3/2007 | Jernigan |
| 2009/0007709 | A1 * | 1/2009 | Sugita et al. ............. 74/411.5 |
| 2011/0209925 | A1 | 9/2011 | Rossi |
| 2012/0004815 | A1 | 1/2012 | Behnke |
| 2012/0253760 | A1 | 10/2012 | Zielke |
| 2013/0000393 | A1 * | 1/2013 | Cash et al. ................. 73/74 |
| 2013/0317696 | A1 | 11/2013 | Koch et al. |
| 2014/0174199 | A1 | 6/2014 | Strnad et al. |
| 2014/0216894 | A1 | 8/2014 | Fourney |
| 2014/0236381 | A1 * | 8/2014 | Anderson et al. ............. 701/1 |
| 2014/0262547 | A1 | 9/2014 | Acheson et al. |
| 2014/0262548 | A1 | 9/2014 | Acheson et al. |

FOREIGN PATENT DOCUMENTS

| | | |
|---|---|---|
| EP | 0960557 A1 | 12/1999 |
| EP | 0960558 B1 | 4/2003 |
| WO | WO-2013023142 A1 | 2/2013 |
| WO | WO-2013028378 A3 | 2/2013 |
| WO | WO-2014143759 A1 | 9/2014 |
| WO | WO-2014149675 A1 | 9/2014 |
| WO | WO-2014151025 A2 | 9/2014 |
| WO | WO-2014151025 A3 | 9/2014 |

OTHER PUBLICATIONS

"Precision Planting YieldSense", [online]. Retrieved from the Internet: <URL: http://www.precisionplanting.com/#products/yieldsense/>, (Published Prior to Mar. 15, 2013), 6 pgs.
"Raven SmartYield Pro", [online]. Retrieved from the Internet: <URL: http://ravenprecision.com/products/harvest-controls/smartyield-pro/>, (Published Prior to Mar. 15, 2013), 3 pgs.
"Trimble Yield Monitoring", [online]. Retrieved from the Internet: <URL: http://www.trimble.com/Agriculture/yield-monitoring.aspx>, (Published Prior to Mar. 15, 2013), 4 pgs.
"U.S. Appl. No. 12/835,054, Preliminary Amendment filed Apr. 18, 2013", 3 pgs.
"International Application Serial No. PCT/US2014/020253, International Search Report mailed May 21, 2014", 2 pgs.
"International Application Serial No. PCT/US2014/020253, Written Opinion mailed May 21, 2014", 7 pgs.
"International Application Serial No. PCT/US2014/024789, International Search Report mailed Jul. 14, 2014", 2 pgs.
"International Application Serial No. PCT/US2014/024789, Written Opinion mailed Jul. 14, 2014", 4 pgs.
"International Application Serial No. PCT/US2014/027861, International Search Report mailed Jul. 21, 2014", 3 pgs.
"International Application Serial No. PCT/US2014/027861, Written Opinion mailed Jul. 21, 2014", 3 pgs.
"U.S. Appl. No. 13/835,054, Non Final Office Action mailed Mar. 6, 2015", 27 pgs.
"U.S. Appl. No. 13/835,099, Non Final Office Action mailed Feb. 24, 2015", 23 pgs.
"International Application Serial No. PCT/US2014/020253, Written Opinion mailed Mar. 6, 2015", 13 pgs.
"U.S. Appl. No. 13/835,054, Examiner Interview Summary mailed Jul. 9, 2015", 3 pgs.
"U.S. Appl. No. 13/835,054, Final Office Action mailed Jul. 22, 2015", 14 pgs.
"U.S. Appl. No. 13/835,054, Response filed Jul. 6, 2015 to Non Final Office Action mailed Mar. 6, 2015", 16 pgs.
"U.S. Appl. No. 13/835,099, Examiner Interview Summary mailed Jul. 23, 2015", 4 pgs.
"U.S. Appl. No. 13/835,099, Final Office Action mailed Jun. 19, 2015", 23 pgs.
"U.S. Appl. No. 13/835,099, Notice of Allowance mailed Aug. 4, 2015", 8 pgs.
"U.S. Appl. No. 13/835,099, Response filed May 26, 2015 to Non Final Office Action mailed Feb. 24, 2015", 15 pgs.
"U.S. Appl. No. 13/835,099, Response filed Jul. 16, 2015 to Final Office Action mailed Jun. 19, 2015", 13 pgs.
"International Application Serial No. PCT/US2014/020253, International Preliminary Report on Patentability mailed Aug. 7, 2015", 13 pgs.
"Weights, Measures, and Conversion Factors for Agricultural Commodities and Their Products", United States Department of Agriculture, Economic Research Service, Agricultural Handbook No. 697, Supersedes SB-616, Conversion Factors and Weights and Measures for Agricultural Commodities and Their Products, 1979, (1979), 77.
Beuerlein, Jim, "Bushels, Test Weights and Calculations", The Ohio State University FactSheet, Department of Horticulture and Crop Science, 2021 Coffey Road, Columbus, Ohio 43210-1044, ohioline.ag.ohio-state.edu—your Link to Information, News, and Education; http://ohioline.osu.edu/agf-fact/0503.html, (Jul. 2, 2015), 2.
"U.S. Appl. No. 13/835,054, Response filed Sep. 24, 2015 to Final Office Action mailed Sep. 24, 2015", 16 pgs.
"U.S. Appl. No. 13/835,054, Non Final Office Action mailed Nov. 12, 2015", 7 pgs.
"Application Serial No. PCT/US2014/024789, International Preliminary Report on Patentability mailed Oct. 29, 2015", 6 pgs.
"U.S. Appl. No. 13/835,099, Non Final Office Action mailed Nov. 24, 2015", 11 pgs.
"U.S. Appl. No. 13/835,099, Response filed Jan. 26, 2016 to Non Final Office Action mailed Nov. 24, 2015", 55 pgs.

* cited by examiner

REMOTE MOISTURE SENSOR AND METHODS FOR THE SAME

CROSS-REFERENCE TO RELATED PATENT DOCUMENTS

This patent application is also related to U.S. patent application Ser. No. 13/835,054, entitled "MULTI-VARIABLE YIELD MONITOR AND METHODS FOR THE SAME"; filed on Mar. 15, 2013, and incorporated herein by reference.

This patent application is also related to U.S. patent application Ser. No. 13/835,099, entitled "HARVESTER ELEVATOR IN-FLOW WEIGHT SENSOR AND METHODS FOR THE SAME"; filed on Mar. 15, 2013, and incorporated herein by reference.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in the drawings that form a part of this document: Copyright Raven Industries, Inc.; Sioux Falls, S.D. All Rights Reserved.

TECHNICAL FIELD

This document pertains generally, but not by way of limitation, to systems and methods of determining crop moisture.

BACKGROUND

Yield monitor systems are used to measure crop yields during harvesting. Yield characteristics, such as one or more of weight or moisture content, are used to assess the quality and quantity of a crop and accordingly determine its purchase price. In one example a yield equation that assesses the quality and quantity of a crop is based on four distinct variables and a fifth related variable. The four variables include volume, temperature, moisture, and test weight (density) of the harvested crop. The fifth related variable is the weight of the harvested crop, and with at least some yield monitors the weight is determined according to the volume and test weight. Additionally, crop moisture content directly affects the crop weight. Further, in some instances there are limitations on acceptable moisture content for specific crops. Accordingly, determining moisture content of a crop is typically conducted prior to selling or purchasing crop.

One example of a moisture sensor used with crop flows includes one or more capacitance plates configured to determine the capacitance of a crop as it passes each of the one or more plates. The measured capacitance signal is conditioned and converted into moisture content.

OVERVIEW

The present inventors have recognized, among other things, that a problem to be solved can include the minimizing of error introduced by current crop moisture measuring techniques. In an example, the present subject matter can provide a solution to this problem, such as by a system or method that measures a crop moisture property while the crop is static relative to a moisture sensor. Stated another way, the crop and moisture sensor are stationary relative to one another, consequently reducing error introduced by fluidity of the crop.

In one example, the systems or methods described herein measure a property corresponding to moisture content of the harvested crop, such as capacitance, as it ascends in a harvester elevator of a combine. This dynamic system allows for moisture content measurement of a crop that moving with and thus static relative to a sensor, while the crop is moved within the harvester elevator. By continuously measuring a moving flow of the harvested crop interruptions in harvesting for sampling and moisture content measurements is avoided. Additionally, error provided by static sensors that measure the moisture content of a moving harvested crop (e.g., flowing past the sensor) are avoided.

Further, in another example, the systems and methods described herein utilize more than one sensor, such that the moisture property of a representative percentage of the harvested crop is determined. Additionally, multiple sensors that move with the harvested crop (e.g., along one or more paddles of an elevator) provide accurate sensing of moisture content and corresponding detection of heterogeneous moisture contents that is not readily available with a moisture sensor configured to measure moisture content from a moving crop flow.

The present inventors have further recognized that a problem to be solved can include error introduced by sensors attempting to measure crop characteristics of a crop moving relative to the sensors. Current moisture sensor methods include moving a crop over a static sensor. Such methods are able to determine moisture content if the crop is homogenous, but struggle with accurately measuring moisture content of a heterogeneous harvested crop. That is, due to small samples sizes of existing systems and methods, heterogeneous moisture content can easily skew (or is alternatively concealed) in the sensed moisture content provided by a static sensor. The present disclosure substantially reduces the error of current systems and methods by measuring the crop while static relative to the sensor. For example, a harvested crop quantity is measured while at rest on a paddle having the moisture sensor thereon, while the paddle ascends in the harvester elevator of a combine.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
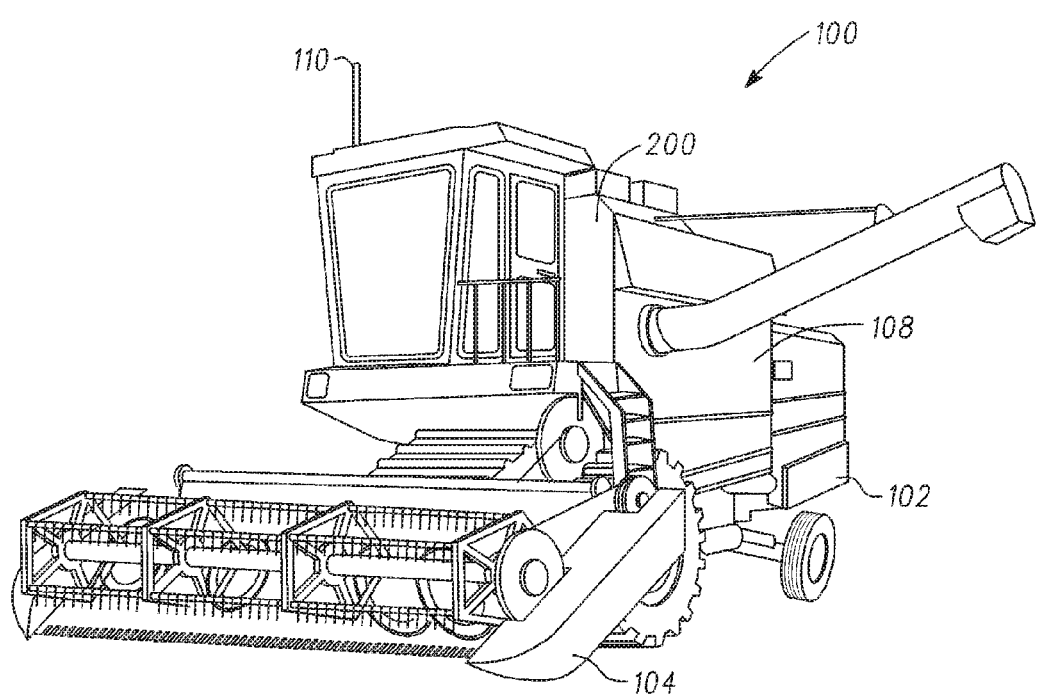
FIG. 1 is perspective view of one example of a harvester.

FIG. 1 shows one example of a harvester such as a harvester combine 100. As shown, the harvester 100 includes a body 102 and a header 104 movably coupled with the body 102. In one example, the header 104 is used to cut and divide crops, such as grain, and deliver the crops into the body 102 for further processing. Referring again to FIG. 1, in one example the harvester 100 includes a harvester elevator 200 configured to remove processed crop, for instance from the internal mechanisms of the harvester 100, and deposit the crop within a crop tank 108. As further shown in FIG. 1, an antenna such as a GPS antenna 110 is further provided on the body 102 to provide accurate position data of the harvester 100 for instance while harvesting within a field.

As previously described the harvester 100 includes a harvester elevator 200 configured to deliver crop from processing into a crop tank 108. As will be described herein the harvester elevator 200 includes one or more sensing instruments, as well as a receiver and processing node configured to measure a crop moisture content of a crop delivered through the harvest elevator 200 to the crop tank 108. As described herein, the crop moisture content measuring system provided herein is configured to measure the crop moisture content of crop harvested from a field. The crop moisture content measurement system is configured to determine the crop moisture content in a dynamic fashion, such as when as the harvester 100 is harvesting the crop within a field.

Figure 2:
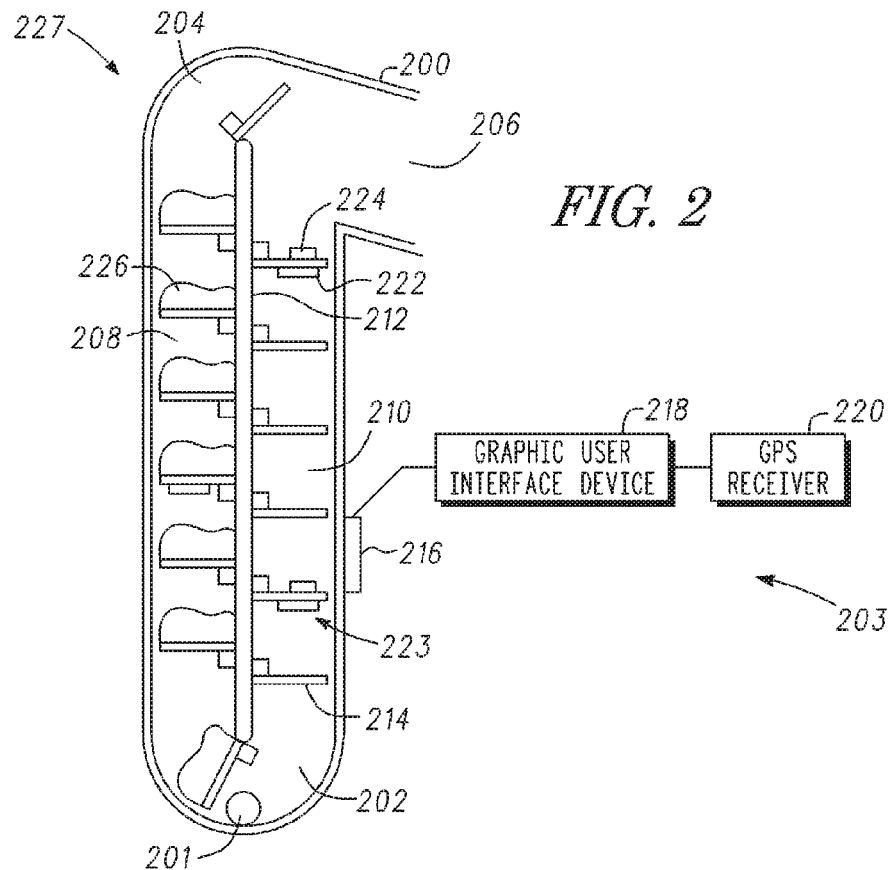
FIG. 2 is a schematic diagram of a remote moisture sensor system.

Referring now to FIG. 2, one example of a harvester elevator 200, which may be used with the system shown in FIG. 1, is provided. In the schematic view provided in FIG. 2, an elevator loop 212 is shown extending through the harvester elevator 200. The elevator loop 212 includes a plurality of paddles 214 arranged in an offset fashion that accordingly move within ascending and descending segments 208, 210. During the descending segment 210 the paddles 214 move without a harvested crop and accordingly engage with a harvested crop, for instance at a trough segment 202. The harvested crop is, in one example, supplied through a supply auger 201 and is engaged by one or more of the paddles 214 as the paddles move through the trough segment 208. The harvested crop, for instance, is a quantity of harvested crop 226, as shown in FIG. 2, which is elevated along the ascending segment 208 of the harvester elevator 200. In one example, the quantity of harvested crop 226 on each of the paddles 214 is substantially static relative to the paddle 214 as it ascends. That is to say, the paddle 214 and the quantity of harvested crop 226 on the respective paddle 214 are substantially static relative to one another while the composites of the quantity of the harvested crop 226 and the paddle 214 are otherwise moving within the ascending segment 208 towards an apex segment 204. The quantity of harvested crop 226 is elevated to the apex segment 204, as previously described, and delivered through a crop chute 206 for instance to the crop tank 108.

As further shown in FIG. 2, one example of a crop moisture content measuring system 227 is provided. In the example shown, the crop moisture content measuring system 227 includes sensing instrument 223 configured to measure moisture content of the harvested crop dynamically, for instance as the harvester 100 is harvesting the crop within a field. In the example shown, the crop moisture content measuring system 227 includes a moisture sensing instrument 223. In the example shown in FIG. 2, the crop moisture sensing instrument 223 includes a moisture sensor 224 and microcontroller 222 associated with one or more of the paddles 214. Stated another way, the crop moisture sensing instrument 223 is installed on one of the paddles 214 (and alternatively a plurality of paddles of the total number of paddles of the elevator loop 212). The harvester elevator 200 includes, for instance, a plurality of crop moisture sensing instruments 223 distributed of the plurality of paddles 214.

As further shown in FIG. 2, the crop moisture content measuring system 227 includes a receiver and processing node 216. The receiver and processing node 216, in one example, serves as the nexus point or communal node for each of the sensing instruments including, for instance, the one or more crop moisture sensing instruments 223, including each crop moisture sensor 224 and microcontroller 222. As further shown in FIG. 2, in one example the receiver and processing node 216 is in communication with the antenna such as the antenna 110 previously shown in FIG. 1. Accordingly, any of the crop characteristics measured with one or more of the crop moisture sensing instruments 223 are associated with the position of the harvester 100, as described herein. Additionally, the cooperation between the antenna 110, the receiver and processing node 216 and one or more of the instruments described herein are used to accordingly determine the harvested crop moisture content and associate that moisture content with a particular location within a field. Stated another way, the crop moisture content measuring system 227 is able to dynamically measure the harvested crop moisture content with the instruments previously described herein and associate the harvested crop moisture content with the corresponding location on a map, such as a yield map including a plurality of zones. By blending this information, for instance with the receiver and processing node 216, a dynamic map of the harvested crop moisture content within the field is accordingly produced.

In another example the crop weight measuring system 227 includes a graphical user interface (GUI) 218 configured to allow user input from an operator. For instance the operator is able to initiate one or more of calibration, diagnostics, and review the sensor inputs and yield outputs communicated to and delivered from the receiver and processing node 216 for instance while the harvester 100 is in a harvesting operation within a field.

The crop moisture content sensing instrument 223 is configured to dynamically measure a moisture content of a quantity of harvested crop delivered through the harvester elevator 200 in a particular time. Accordingly the instrument 223 is able to dynamically measure the harvested crop moisture content as the characteristic changes, for instance as the harvester 100 moves through different areas of the field having a frame production (e.g., yield) of a particular harvested crop. That is to say, the crop moisture sensing instrument 223 is able to dynamically measure crop moisture content as a particular quantity of crop is moving through the harvester elevator 200. Accordingly, as crop moisture content changes throughout the field the instruments 223 in cooperation with receiver and processing node 216 are able to measure and log the corresponding crop moisture content.

Figure 3:
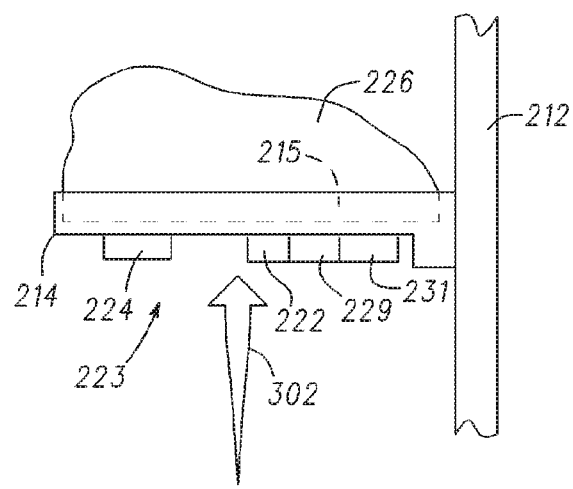
FIG. 3 is a schematic diagram of a paddle mounted remote moisture sensor.

Referring now to FIG. 3, one example of the crop moisture content sensing instrument 223 is provided. As previously shown in FIG. 2, a crop moisture content sensing instrument 223, including the moisture sensor 224 and microcontroller 222, can be installed on each of the paddles 214 moving in the ascending segment 208 toward the apex 204, such as in the direction 302. In other embodiments, the system 227 can include a crop moisture content sensing instrument 223 on fewer than each of the paddles 214. For example, every other paddle 214 may include an instrument 223 or only one paddle 214 may include a sensing instrument 223.

One example of such a paddle 214 with the quantity of harvested crop 226 is provided in FIG. 3. For instance, the harvested crop 226 can rest on a surface of the paddle 214 or can rest within a cavity 215 configured to hold or support the harvested crop 226 as the paddle 214 ascends 302 in the ascending segment 208. As shown, the crop moisture content sensing instrument 223 includes a moisture sensor 224 positioned within or adjacent to the paddle 214. The moisture sensor 224, includes, but is not limited to, one or more types of moisture sensors, such as a frequency domain sensor, a capacitance sensor, a neutron moisture gauge, time domain transmission, time domain reflectometry, and the like. The moisture sensor 224, for instance, includes a probe that extends into the harvested crop quantity 226. Alternatively, the moisture sensor 224 includes one or more sensors, such as two plates separated by a predefined distances, configured to contact the harvested crop quantity 226 and send a current through the harvested crop 226. The moisture sensing instrument 223 includes a moisture sensor 224, such as a probe and driver electronics, as well as the microcontroller 222. The probe uses changes in capacitance of the harvested crop quantity 226 to sense changes in distances to a target, such as between to plates as is commonly understood in the art. The driver electronics convert the sensed changes in distance from capacitance into voltage changes, which are in turn communicated to the microcontroller 222. An increase in voltage changes indicates, for instance, a greater moisture content of the harvested crop 226.

As further shown in FIG. 3 the crop moisture content sensing instrument 223, in another example, includes a microcontroller 222 in communication with the moisture sensor 224. The microcontroller 222 is powered in one example by a power source 229 for instance including a battery capacitor charged for instance by the movement of the paddle 214 within the harvester elevator 200 and the like. As further shown in FIG. 3 the microcontroller 222 is in one example coupled with a transmitter 231, such as a radio or wireless transmitter. The transmitter 231 facilitates communication between the crop moisture content sensing instrument 223 and the receiver and processing node 216. Accordingly, the moving crop moisture content sensing instrument 223 is able to deliver the measured moisture content of a quantity of the harvested crop 226 to the receiver and processing node 216 even while ascending through the ascending segment 208.

The crop moisture content sensing instrument 223 shown in FIG. 3 is able to determine a static moisture content of the quantity of harvested crop 226. For instance, as the paddle 214 ascends through the ascending segment 208, the quantity of harvested crop 226 is static relative to the paddle 214. Accordingly, any moisture content determinations made with the crop moisture content sensing instrument 223 are not subject to dynamic loading of the quantity of harvested crop 226 (for instance as is the case with the harvested crop impacting an impact plate). Instead, the quantity of the harvested crop 226 is statically positioned on the paddle 214 and accordingly the moisture sensor 224 is able, for instance within the ascending segment 208, to conduct one or more moisture measurements and thereby accurately determine the moisture content of the quantity of harvested crop 226 and deliver the crop moisture content to the receiver and processing node 216.

Figure 4:
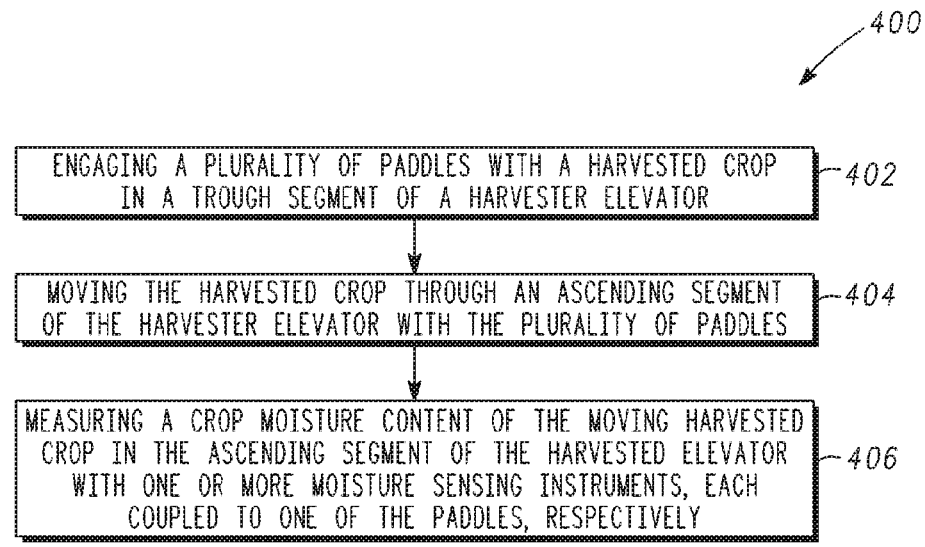
FIG. 4 is a block diagram showing one example of a method for determining moisture of a crop.

FIG. 4 shows a block diagram illustrating one example of a method 400 for measuring crop moisture. In describing the method 400 reference is made to features and elements previously described herein, including numbered references. Numbered elements provided within the description of the method 400 are not intended to be limiting, instead numbered references are provided for convenience and further include any similar features described herein, as well as their equivalents. At 402, the method 400 includes engaging the plurality of paddles 214 with the harvested crop 226 in the trough segment 202 of the harvester elevator 200. For instance, as previously described herein, the harvester elevator 200 includes the plurality of paddles 214 moving along an elevator loop 212 within the elevator shaft 228 and through the trough segment 202, ascending segment 208, apex segment 204, and descending segment 210. Harvested crop 226 is scooped or pushed upward through the trough segment 202 toward the ascending segment 208, such that the harvested crop 226 is contained on or within a portion of the paddle 214.

At 404, the harvested crop 226 is moved through the ascending segment 208 of the harvesting elevator 200 with the plurality of paddles 214. The elevator loop 212 includes a belt, chain, or similar mechanisms to move the paddles 214, such as while the harvester 100 (e.g., combine) is in motion, throughout the elevator shaft 228. Moving the harvested crop, for instance, includes moving the harvested crop static to the paddle within the ascending segment. That is, the relative velocity of the harvested crop to the paddle on which the harvested crop is situated is substantially zero. However, the moving crop within the ascending segment has a velocity relative to the trough segment of the harvester elevator.

At 406, the method 400 includes measuring a crop moisture content of the moving harvested crop 226 in the ascending segment 208 of the harvester elevator 200 with one or more moisture sensing instruments 223, each coupled to one of the plurality of paddles 214, respectively. Measuring can, for example, include continuously measuring the crop moisture content of the harvested crop with at least one of the one or more moisture sensing instruments coupled to one of the plurality of paddles moving the harvested crop through the ascending segment. For instance, the plurality of paddles are distributed in a configuration that positions at least one of the plurality of paddles and one of the moisture sensing instruments within the ascending segment through operation of the harvester elevator. That is, the moisture sensing instruments can be arranged in the elevator loop such that, at any given time, there is a moisture sensing instrument in the ascending segment of the harvester elevator. Continuously measuring the crop moisture content includes measuring the crop moisture content, for instance, during operation of the harvester elevator, when harvested crop is present in the ascending segment.

In an example, the moisture sensor 223 records a capacitance which is then manipulated into a voltage rating. The voltage rating then, according to algorithms, is translated into a moisture content of the harvested crop, such as a weight percentage of moisture.

In an example, the moisture content is measured when a quantity of harvested crop, such as the quantity of harvested crop on a paddle with a moisture sensing instrument, is static relative to one of the one or more moisture sensing instruments in the ascending segment within the harvester elevator, as described herein. In another example, measuring includes sensing a capacitance of the harvested crop, as described herein.

Several options for the method 400 are provided below. In one example, one or more moisture sensor 224 of the one or more moisture sensing instruments 223 are powered down when located and moving along the descending segment of the harvester elevator. Such an example can provide energy efficiency, as well as mitigate stray moisture content measurements that occur in the descending segment. Further, the one or more moisture sensing instruments are triggered to measure the crop moisture content of the harvested crop in the ascending segment. For instance, a position sensor, a static moisture sensor, or an ascendance sensor is configured to trigger the moisture sensing instrument, as described herein. In one example, the measured crop moisture content is correlated to locations on a field, as described herein.

Figure 5:
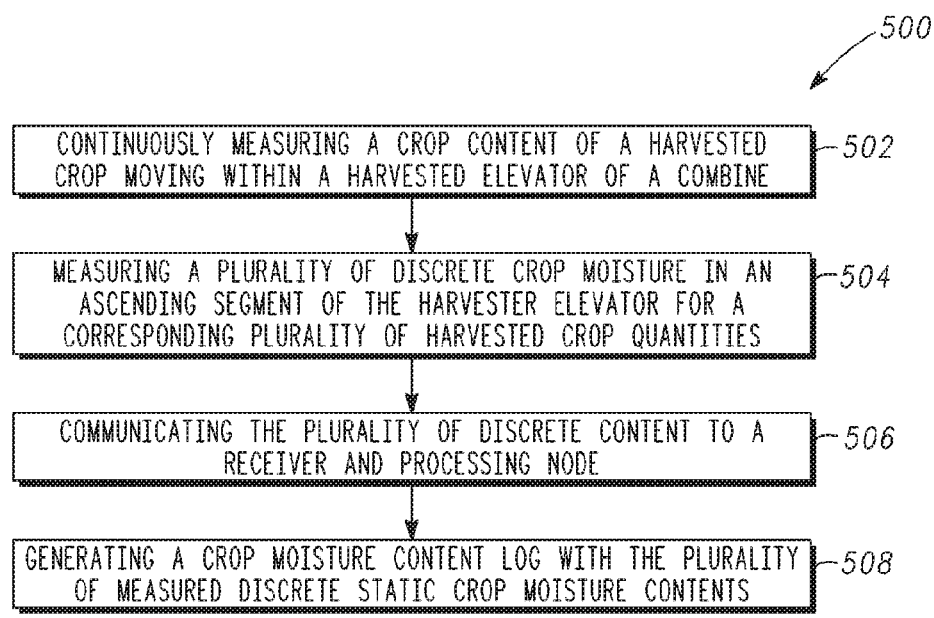
FIG. 5 is a block diagram showing an alternative example of a method for determining moisture of a crop.

FIG. 5 shows a block illustrating one example of a method 500 for determining moisture of a crop. In describing the method 500 reference is made to features and elements previously described herein, including numbered references. Numbered elements provided within the description of the method 500 are not intended to be limiting, instead numbered references are provided for convenience and further include any similar features described herein, as well as their equivalents. At 502, the method 500 includes continuously measuring a crop moisture content of a harvested crop moving within a harvester elevator of a combine. For instance, continuously measuring includes measuring with at least one moisture sensor of one of the plurality of paddles within the ascending segment at any given time during operation of the harvester elevator.

At 504, the method 500 includes measuring a plurality of discrete crop moisture contents in an ascending segment of the harvester elevator for a corresponding plurality of harvested crop quantities. Each of the plurality of the discrete harvested crop quantities, for instance, are static relative to each of a plurality of paddles and instruments coupled with the paddles within the harvester elevator, as described herein. Further, as described herein, each of the plurality of instruments includes a moisture sensor configured to measure one of the discrete crop moisture contents of the harvested crop quantities. For instance, measuring the plurality of discrete crop moisture contents includes measuring the plurality of discrete crop moisture contents during at least a portion of travel of the corresponding paddle along the ascending segment. That is, the discrete crop moisture content can be measured at a bottom, middle, or top portion of the ascending segment, such that the corresponding harvested crop quantity is static relative to the paddle on which the harvested crop quantity is positioned.

At 506, the method 500 includes communicating the plurality of discrete crop moisture contents to a receiver and processing node. At 508, the method 500 includes generating a crop moisture content log with the plurality of measure discrete static crop moisture contents.

In an example, the method 500 includes generating a harvested crop moisture content map, including associating the plurality of measured discrete crop moisture contents with corresponding filed locations, as described herein.

In an example, the method includes determining an overall crop moisture content of the harvested crop from the discrete crop moisture contents. For instances, a standard interpolation algorithm is used to estimate the overall crop moisture at any point during the operation of the harvester elevator. If, for instance, multiple discrete crop moisture contents measurements are available over a predetermined time interval, the multiple measurements are blended by a weighted average, such as averaging the multiple moisture values by the grain flow estimated by a yield monitoring system at the point in time of each discrete crop moisture content measurement.

Figure 6:
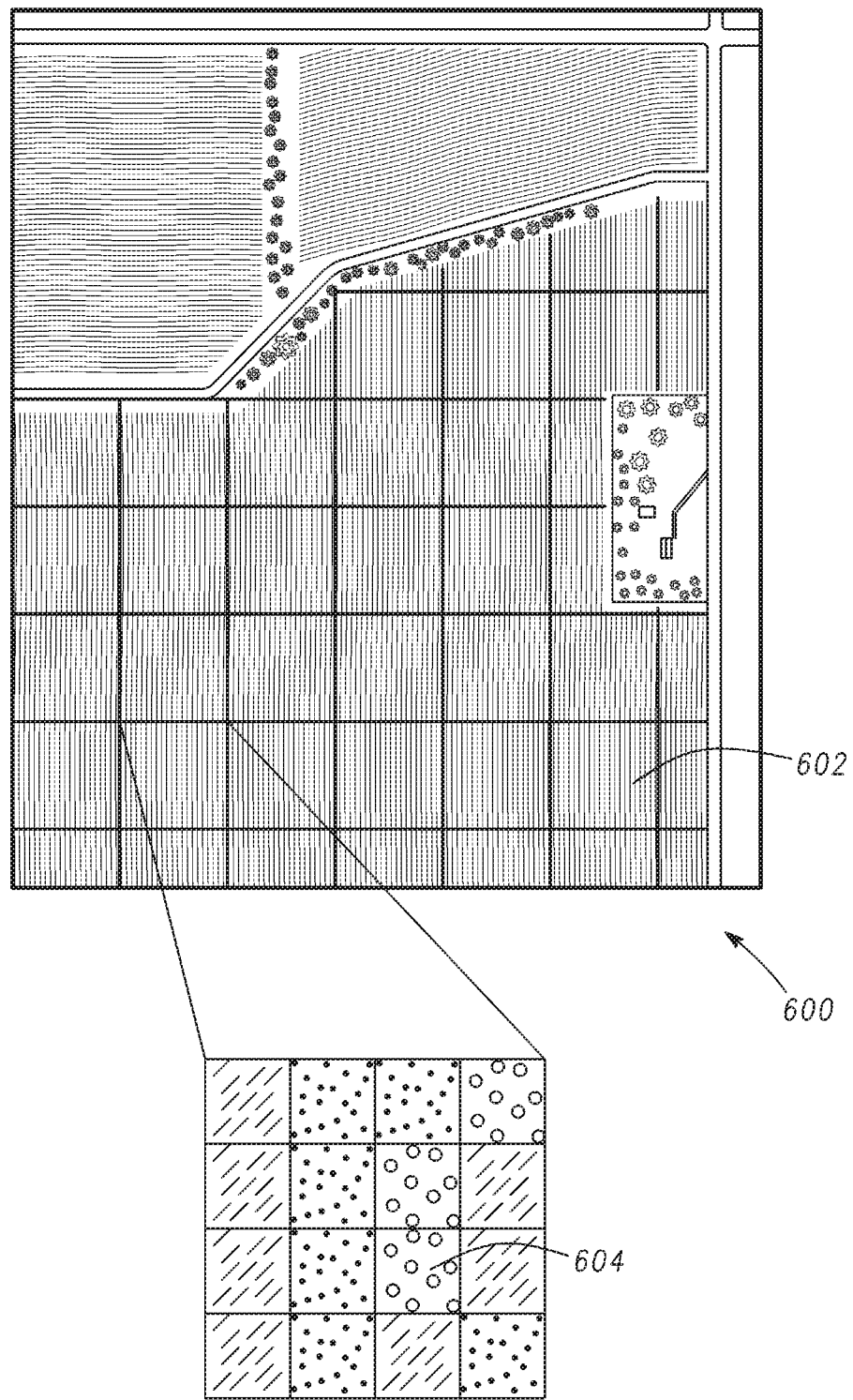
FIG. 6 is one example of a field moisture content map including crop moisture content values associated with corresponding field locations.

FIG. 6 is a demonstrative example of a yield map 600. Optionally the yield map 600 includes but is not limited to providing a visual representation of the dynamic measured harvested crop moisture content. A zoomed in portion of the yield map 600 is shown in the bottom view of FIG. 6. As shown by way of varying stippling, shading or the like a plurality of zones 602 accordingly has corresponding harvested crop moisture contents. For instance, as shown in FIG. 6 a plurality of zones 602 having varying crop moisture contents according to actual measured data for instance provided by the moisture sensing instrument 223 shown in FIGS. 2 and 3 are associated with the one or more zones 602. Accordingly each of the zones 602 includes in one example an array of information including harvested crop moisture contents. The yield map 600 accordingly provides a representation to the operator of the harvested output provided during a harvesting operation. Information provided by the yield map 600 is optionally used for instance to determine better husbandry techniques, planting strategies and the like for the field in the next season.

Referring again to FIG. 6, the plurality of zones 602 include sub-zones 604. As shown, each of the zones and sub-zones has different stippling, shading or the like associated with the harvested crop moisture content measurements. Optionally the sub-zones 604 (or any of the plurality of zones 602) have varying stippling, shading or coloring techniques or any combination thereof to accordingly provide indications of the harvested crop moisture content. As shown in FIG. 6 by way of the stippling, shading, coloring or the like the harvested moisture content varies between each of the zones 602. As shown for instance, each of the sub-zones 604 the stippling is different between the zones thereby indicating measured crop moisture content there between varies. Optionally the yield map 600 provides one or more interactive zones 602. For instance the user is able to zoom in and examine each of the zones 602 accordingly allowing for instance through a graphical user interface interaction with the field map 600 to accordingly determine the crop moisture content of one or a plurality of the zones 602.

VARIOUS NOTES & EXAMPLES

Example 1 can include subject matter (such as an apparatus, a method, a means for performing acts, or a machine readable medium including instructions that, when performed by the machine, that can cause the machine to perform acts), such as a system for measuring crop moisture content in a harvester elevator having paddles for moving crop in an ascending segment, comprising: a receiver and processing node; one or more moisture sensing instruments, each of the one or more instruments including: a moisture sensor configured for coupling with a portion of the paddle, and a transmitter in communication with the receiver and processing node; and wherein each moisture sensing instrument is coupled with a respective one of the paddles of the harvester elevator so that the each moisture sensing instrument moves with the respective paddle to measure a crop moisture content of a harvested crop as the harvested crop moves along the ascending segment of the harvester elevator.

Example 2 can include, or can optionally be combined with the subject matter of Example 1 to optionally include wherein the harvester elevator further comprises an elevator loop having a plurality of paddles, and the plurality of paddles are configured to move about the elevator loop in an elevator loop cycle.

Example 3 can include, or can optionally be combined with the subject matter of one or any combination of Examples 1 or 2 to optionally include wherein the one or more moisture sensing instruments are distributed in the plurality of paddles of the elevator loop to have at least one moisture sensor in the ascending segment at any given time.

Example 4 can include, or can optionally be combined with the subject matter of one or any combination of Examples 1-3 to optionally include comprising at least two moisture sensing instruments coupled with at least two respective paddles of the plurality of paddles, and the at least two respective paddles are distributed on the elevator loop to continually measure the crop moisture content of the harvested crop ascending along the ascending segment.

Example 5 can include, or can optionally be combined with the subject matter of one or any combination of Examples 1-4 to optionally include wherein the one or more moisture sensors are configured to measure the crop moisture content of the harvested crop when a quantity of the harvested crop is static relative to the corresponding moisture sensor and ascending within the harvest elevator.

Example 6 can include, or can optionally be combined with the subject matter of one or any combination of Examples 1-5 to optionally include wherein each moisture sensor of the one or more instruments is configured to measure the moisture content of a heterogeneous harvested crop.

Example 7 can include, or can optionally be combined with the subject matter of one or any combination of Examples 1-6 to optionally include wherein the one or more moisture sensing instruments includes: a microprocessor configured to manipulate the plurality of crop moisture content measurements; a power source configured to power the moisture sensor; and an activation trigger configured to activate the power source and initiate sensing of the moisture sensor.

Example 8 can include, or can optionally be combined with the subject matter of one or any combination of Examples 1-7 to optionally include wherein each of the one or more moisture sensing instruments includes: a deactivation trigger configured to power down the moisture sensor while the corresponding paddle is moving along a descending segment of the harvester elevator; and an activation trigger configured to power on the moisture sensor while the corresponding paddle is moving along the ascending segment of the harvester elevator.

Example 9 can include, or can optionally be combined with the subject matter of one or any combination of Examples 1-8 to optionally include comprising a measurement trigger in communication with the one or more moisture sensing instruments, the measurement trigger configured to initiate sensing with the moisture sensor in the ascending segment.

Example 10 can include, or can optionally be combined with the subject matter of one or any combination of Examples 1-9 to optionally include wherein the measurement trigger includes at least one of a position sensor, a static moisture sensor, and an ascendance sensor configured for coupling with at least one of a paddle or a static portion of the harvester elevator within the ascending segment.

Example 11 can include, or can optionally be combined with the subject matter of one or any combination of Examples 1-10 to optionally include wherein the measurement trigger includes near field communication.

Example 12 can include, or can optionally be combined with the subject matter of one or any combination of Examples 1-11 to include, subject matter (such as an apparatus, a method, a means for performing acts, or a machine readable medium including instructions that, when performed by the machine, that can cause the machine to perform acts), such as can include a method for measuring crop moisture comprising: engaging a plurality of paddles with a harvested crop in a trough segment of a harvester elevator; moving the harvested crop through an ascending segment of the harvester elevator with the plurality of paddles; and measuring a crop moisture content of the moving harvested crop in the ascending segment of the harvester elevator with one or more moisture sensing instruments, each coupled to one of the plurality of paddles, respectively.

Example 13 can include, or can optionally be combined with the subject matter of one or any combination of Examples 1-12 to optionally include comprising continuously measuring the crop moisture content of the harvested crop with at least one of the one or more moisture sensing instruments coupled to one of the plurality of paddles moving the harvested crop through the ascending segment.

Example 14 can include, or can optionally be combined with the subject matter of one or any combination of Examples 1-13 to optionally include wherein the plurality of paddles of the harvester elevator are distributed in a configuration that positions at least one of the plurality paddles and one of the one or more moisture sensing instruments within the ascending segment throughout operation of the of the harvester elevator, and wherein measuring the crop moisture content includes continuously measuring the crop moisture content of the harvested crop in the ascending segment.

Example 15 can include, or can optionally be combined with the subject matter of one or any combination of Examples 1-14 to optionally include comprising measuring the crop moisture content of the harvested crop when a quantity of the harvested crop is static relative to one of the one or more moisture sensing instruments and ascending within the harvester elevator.

Example 16 can include, or can optionally be combined with the subject matter of one or any combination of Examples 1-15 to optionally include comprising powering down at least one of the one or more moisture sensors of the moisture sensing instrument when the at least one moisture sensors is moving along a descending segment of the harvester elevator.

Example 17 can include, or can optionally be combined with the subject matter of one or any combination of Examples 1-16 to optionally include comprising triggering at least one of the one or more moisture sensing instruments to measure the crop moisture content of the harvested crop in the ascending segment.

Example 18 can include, or can optionally be combined with the subject matter of one or any combination of Examples 1-17 to optionally include comprising corresponding each of the measured crop moisture contents to a location on a field.

Example 19 can include, or can optionally be combined with the subject matter of one or any combination of Examples 1-18 to include, subject matter (such as an apparatus, a method, a means for performing acts, or a machine readable medium including instructions that, when performed by the machine, that can cause the machine to perform acts), such as can include a method for measuring in-flow moisture of a harvested crop comprising: continuously measuring a crop moisture content of a harvested crop moving within a harvester elevator of a combine, continuously measuring including: measuring a plurality of discrete crop moisture contents in an ascending segment of the harvester elevator for a corresponding plurality of harvested crop quantities, each of the plurality of the harvested crop quantities is static relative to each of a plurality of paddles and instruments coupled with the paddles within the harvester elevator, each of the plurality of instruments include a moisture sensor, the moisture sensor configured to measure one of the discrete crop moisture contents of the harvested crop quantities; communicating the plurality of discrete crop moisture contents to a receiver and processing node; and generating a crop moisture content log with the plurality of measured discrete static crop moisture contents.

Example 20 can include, or can optionally be combined with the subject matter of one or any combination of Examples 1-19 to optionally include comprising generating a harvested crop moisture content map, including associating the plurality of measured discrete crop moisture contents with corresponding field locations.

Example 21 can include, or can optionally be combined with the subject matter of one or any combination of Examples 1-20 to optionally include wherein continuously measuring includes measuring with at least one moisture sensor of one of the plurality of paddles within the ascending segment at any given time during operation of the harvester elevator.

Example 22 can include, or can optionally be combined with the subject matter of one or any combination of Examples 1-21 to optionally include comprising determining an overall crop moisture content of the harvested crop from the plurality of discrete crop moisture contents.

Example 23 can include, or can optionally be combined with the subject matter of one or any combination of Examples 1-22 to optionally include wherein measuring the plurality of discrete crop moisture contents includes measuring the plurality of discrete crop moisture contents during all or a portion of travel along the ascending segment.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system for measuring crop moisture content in a harvester elevator having ascending paddles for moving crop in an ascending segment, comprising:
    a receiver and processing node;
    one or more moisture sensing instruments, each of the one or more instruments including:
        a moisture sensor configured for coupling with a portion of the ascending paddle, and
        a transmitter in communication with the receiver and processing node; and
    wherein each moisture sensing instrument is coupled with a respective one of the ascending paddles of the harvester elevator so that the each moisture sensing instrument moves with the respective ascending paddle to measure a crop moisture content of a harvested crop as the harvested crop moves along the ascending segment of the harvester elevator.

2. The system of claim 1, wherein the harvester elevator further comprises an elevator loop having a plurality of ascending paddles, and the plurality of ascending paddles are configured to move about the elevator loop in an elevator loop cycle.

3. The system of claim 2, wherein the one or more moisture sensing instruments are distributed in the plurality of ascending paddles of the elevator loop to have at least one moisture sensor in the ascending segment at any given time.

4. The system of claim 2 comprising at least two moisture sensing instruments coupled with at least two respective ascending paddles of the plurality of ascending paddles, and the at least two respective ascending paddles are distributed on the elevator loop to continually measure the crop moisture content of the harvested crop ascending along the ascending segment.

5. The system of claim 1, wherein the one or more moisture sensors are configured to measure the crop moisture content of the harvested crop when a quantity of the harvested crop is static relative to the corresponding moisture sensor and ascending within the harvest elevator.

6. The system of claim 1, wherein each moisture sensor of the one or more instruments is configured to measure the moisture content of a heterogeneous harvested crop.

7. The system of claim 1, wherein the one or more moisture sensing instruments includes:
 a microprocessor configured to manipulate the plurality of crop moisture content measurements;
 a power source configured to power the moisture sensor; and
 an activation trigger configured to activate the power source and initiate sensing of the moisture sensor.

8. The system of claim 1, wherein each of the one or more moisture sensing instruments includes:
 a deactivation trigger configured to power down the moisture sensor while the corresponding paddle is moving along a descending segment of the harvester elevator; and
 an activation trigger configured to power on the moisture sensor while the corresponding paddle is moving along the ascending segment of the harvester elevator.

9. The system of claim 1 comprising a measurement trigger in communication with the one or more moisture sensing instruments, the measurement trigger configured to initiate sensing with the moisture sensor in the ascending segment.

10. The system of claim 9, wherein the measurement trigger includes at least one of a position sensor, a static moisture sensor, and an ascendance sensor configured for coupling with at least one of an ascending paddle or a static portion of the harvester elevator within the ascending segment.

11. The system of claim 9, wherein the measurement trigger includes near field communication.

12. A method for measuring crop moisture comprising:
 engaging a plurality of ascending paddles with a harvested crop in a trough segment of a harvester elevator;
 moving the harvested crop through an ascending segment of the harvester elevator with the plurality of ascending paddles; and
 measuring a crop moisture content of the moving harvested crop in the ascending segment of the harvester elevator with one or more moisture sensing instruments, each coupled to one of the plurality of ascending paddles, respectively, and
 powering down at least one of the one or more moisture sensors of the moisture sensing instrument when the at least one moisture sensors is moving along a descending segment of the harvester elevator.

13. The method of claim 12 comprising continuously measuring the crop moisture content of the harvested crop with at least one of the one or more moisture sensing instruments coupled to one of the plurality of ascending paddles moving the harvested crop through the ascending segment.

14. The method of claim 12, wherein the plurality of ascending paddles of the harvester elevator are distributed in a configuration that positions at least one of the ascending plurality paddles and one of the one or more moisture sensing instruments within the ascending segment throughout operation of the of the harvester elevator, and
 wherein measuring the crop moisture content includes continuously measuring the crop moisture content of the harvested crop in the ascending segment.

15. The method of claim 12 comprising measuring the crop moisture content of the harvested crop when a quantity of the harvested crop is static relative to one of the one or more moisture sensing instruments and ascending within the harvester elevator.

16. The method of claim 12 comprising triggering at least one of the one or more moisture sensing instruments to measure the crop moisture content of the harvested crop in the ascending segment.

17. The method of claim 12 comprising corresponding each of the measured crop moisture contents to a location on a field.

* * * * *